(12) United States Patent
Monassevitch

(10) Patent No.: US 6,171,320 B1
(45) Date of Patent: Jan. 9, 2001

(54) SURGICAL CLIP

(75) Inventor: Leonid Monassevitch, Katzrin (IL)

(73) Assignee: Niti Alloys Technologies Ltd., Katzrin (IL)

( * ) Notice: Under 35 U.S.C. 154(b), the term of this patent shall be extended for 0 days.

(21) Appl. No.: 09/308,603

(22) PCT Filed: Oct. 7, 1997

(86) PCT No.: PCT/IL97/00325

§ 371 Date: May 20, 1999

§ 102(e) Date: May 20, 1999

(87) PCT Pub. No.: WO98/29040

PCT Pub. Date: Jul. 9, 1998

(30) Foreign Application Priority Data

Dec. 25, 1996 (IL) .................................................. 119911

(51) Int. Cl.[7] .................................................. A61B 17/08
(52) U.S. Cl. .................................................. 606/151
(58) Field of Search .................................................. 606/151, 153, 606/139, 219, 142–143; 227/175–182

(56) References Cited

U.S. PATENT DOCUMENTS 5,171,252  12/1992  Friedland .
5,382,260   1/1995  Dormandy, Jr., et al. .
5,540,701   7/1996  Sharkey et al. .
5,582,616 * 12/1996  Bolduc .................................. 606/143

FOREIGN PATENT DOCUMENTS 0 326 757 B1  7/1993  (EP) .
  1186199    10/1985  (SU) .

* cited by examiner

Primary Examiner—Michael Buiz
Assistant Examiner—Hoa B. Trinh
(74) Attorney, Agent, or Firm—Pearne & Gordon LLP

(57) ABSTRACT

This invention is a surgical clip (10) including three lengths of wire integrally formed of a shape memory alloy, two of which (12, 22) each form closed geometrical shapes similar in configuration and magnitude to each other, and the third (18) connects the first two. When at a first temperature or higher, the first and second lengths of wire (12, 22) are positioned in a side by side closed position. The shape memory alloy is in an elastic sate. When at a second temperature or lower, below the first temperature, the shape memory alloy is in a plastic state, thereby enabling the first and second lengths of wire (12, 22) to be moved into and to retain a spaced apart position. Upon heating of the clip to a temperature at least equal to the first temperature, the first and second lengths of wire return to the side by side closed position, thereby to apply a compressive force to tissue located therebetween; and a method of anastomosing a gastrointestinal tract with such a surgical clip (10).

14 Claims, 3 Drawing Sheets

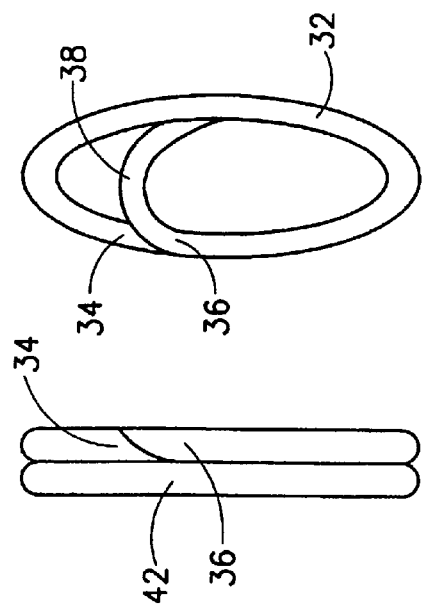
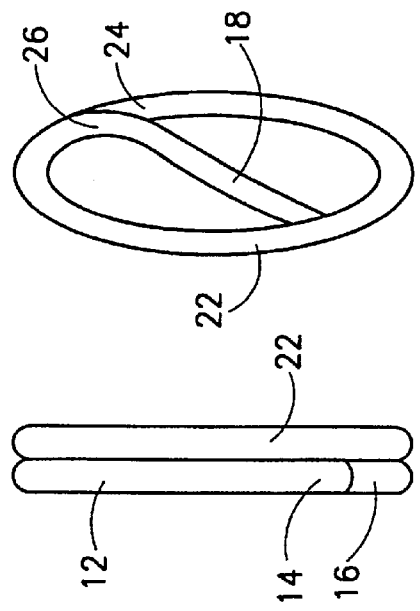
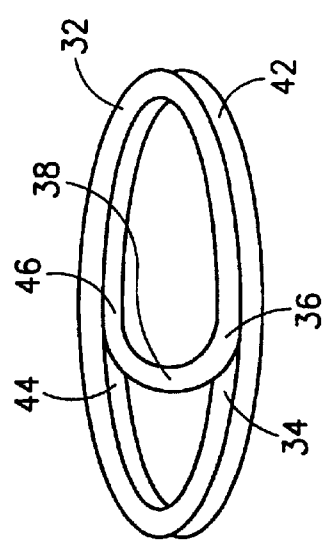
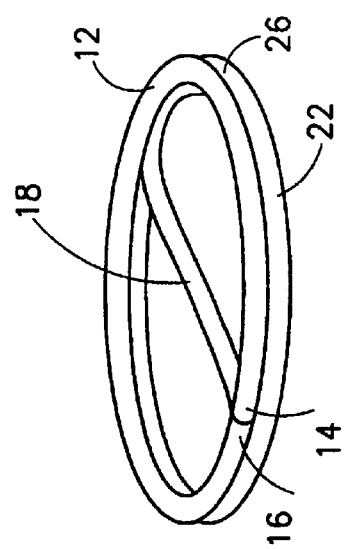

SURGICAL CLIP

FIELD OF THE INVENTION

The present invention relates to the field of surgical clips generally, and, in particular, to the field of surgical clips formed of a shape memory alloy.

BACKGROUND OF THE INVENTION

Several methods are known in the art for joining portions of hollow organs, such as the gastrointestinal tract. These include threads for manual suturing, staplers for mechanical suturing, and compression rings and clips.

While manual suturing is universally known and relatively inexpensive, the degree of success depends considerably on the skill of the surgeon. Another disadvantage is that post-operative complications are common. Further, suturing an organ results in lack of smoothness of the tissue therein, which, when the sutured organ is part of the gastrointestinal tract, hampers peristalsis in the sutured area. Finally, suturing is both labor and time consuming.

Staplers for mechanical suturing ensure a reliable joining of tissue and enable the time needed for surgery to be reduced, compared with manual suturing. However, due to the facts that such staples are not reusable and that a great many types and sizes are required, the price of staples is high. Also, after healing, metal staples remain in place along the perimeter of the suture, which reduces elasticity of the junction and adversely affects peristalsis when the sutured organ is part of the gastrointestinal tract.

Junctions using compression devices such as rings and clips ensure the best seal and post-operative functioning of the organs. Two types of compression devices are known, namely, rings made of resorption plastics and clips made of memory alloys. Plastic rings are cumbersome and expensive. Also, the compression force is applied only momentarily at the junction and is reduced as the tissue is crushed. Clips made of memory alloys enable portions of tissue to be pressed together with increasing pressure as they are heated, due to the inherent properties of the alloys.

Development of clips made of memory alloy materials has increased recently, as they have many advantages over other devices. Their design is simple, they are cheap, they are small in size and possess universal qualities, and they are self-evacuated from the gastrointestinal tract.

It is known in the art to provide a surgical fastening clip which applies a clamping force to a site, such as a blood vessel, thereby reducing its cross-sectional area. It is also known to provide a surgical fastening clip formed of a shape memory alloy which deforms to a closed configuration when heated, such that the clamping force applied thereby is increased as it is heated. For example, U.S. Pat. No. 5,171,252 discloses a surgical fastening clip formed of a shape memory alloy; the device disclosed therein includes separate legs which close tightly around a site. Such a device is limited in its uses, such as for clamping blood vessels, and is not suitable for joining portions of the gastrointestinal tract.

EP 0,326,757 discloses a device for anastomosing a digestive tract, which includes a plurality of U-shaped retaining clips disposed around a soluble support tube. The tube is positioned inside portions of the digestive tract to be joined, and includes an outer groove around which are disposed the U-shaped retaining clips. The retaining clips are made of a shape memory alloy such that the open ends thereof close at a predetermined temperature, thus joining ends of the digestive tract. Once the ends of the digestive tract have been joined, the tube is dissolved. Such a device is disadvantageous in that its use requires that a plurality of clips to be properly positioned simultaneously. Also, there is no assurance that the resulting junction will be smooth, due to the plurality of sites of the digestive tract joined by the plurality of clips.

SU 1,186,199 discloses a memory alloy clip consisting of two parallel coils to be used for joining portions of a hollow organ, such as an organ of the gastrointestinal tract. The portions of the organ to be joined are aligned, and each of the plastic coils is introduced through a puncture formed in the wall of one of the portions. The coils are positioned such that, when heated, they compress the aligned walls therebetween, thus maintaining the portions of the walls held within the loops of the coils adjacent each other. Thereafter, incisions are made through the portions of the walls held within the loops of the coils, such that a passageway is created between the two organ portions. The punctures in the organ walls must then be surgically sewn closed with interrupted surgical sutures.

A major disadvantage of known memory alloy clips is that they permit compression of only approximately 80–85% of the junction perimeter, thus requiring additional manual sutures, which reduce the seal of the junction during the healing period and its elasticity during the post-operative period. Furthermore, this additional suturing is problematic inasmuch as it has to carried out across a joint which includes a portion of the clip, thereby rendering difficult the sealing and anastomosis of the organ portions.

SUMMARY OF THE INVENTION

The present invention seeks to provide an improved surgical clip formed of a shape memory alloy, and a method of joining two portions of a hollow organ, which overcome disadvantages of prior art.

There is thus provided, in accordance with a preferred embodiment of the present invention, a surgical clip which includes:

a first length of a wire formed of a shape memory alloy and having first and second end portions which overlap so as to form a closed geometrical shape having a central opening;

a second length of a wire formed of the shape memory alloy and having first and second end portions which overlap so as to form a closed geometrical shape similar in configuration and magnitude to the first length of wire, wherein, when placed in side-by-side registration, the first and second lengths of wire fully overlap but the second end portions thereof do not overlap; and a third length of a wire of the shape memory alloy and formed integrally with the second end portions of the first and second lengths of wire thereby to extend across the central opening so as to connect together the first and second lengths of wire;

wherein when at a first temperature or higher, the first and second lengths of wire are positioned in a side-by-side closed position and the shape memory alloy is in an elastic state, and further, when at a second temperature or lower, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-byside closed position, thereby to apply a compressive force to tissue located therebetween.

Additionally in accordance with a preferred embodiment of the invention, the geometrical shape is an ellipse.

Further in accordance with a preferred embodiment of the invention, as S-shaped length is defined by the second end of the first length of wire, the third length of wire, and the second end of the second length of wire.

Additionally in accordance with a preferred embodiment of the invention, a C-shaped length is defined by the second end of the first length of wire, the third length of wire, and the second end of the second length of wire.

In accordance with a further embodiment of the invention, there is provided a method for anastomosing a gastrointestinal tract, the method including the following steps:

(a) providing a surgical clip which has a first length of a wire formed of a shape memory alloy and having first and second end portions which overlap so as to form a closed geometrical shape having a central opening; a second length of a wire formed of the shape memory alloy and having first and second end portions which overlap so as to form a closed geometrical shape similar in configuration and magnitude to the first length of wire, wherein, when placed in side-by-side registration, the first and second lengths of wire fully overlap but the second end portions thereof do not overlap; and a third length of a wire of the shape memory alloy and formed integrally with the second end portions of the first and second lengths of wire thereby to extend across the central opening so as to connect together the first and second lengths of wire; wherein when at a first temperature or higher, the first and second lengths of wire are positioned in a side-by-side closed position and the shape memory alloy is in an elastic state, and further, when at a second temperature or lower, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-by-side closed position, thereby to apply a compressive force to tissue located therebetween;

(b) cooling the clip to a temperature below its phase transition temperature;

(c) manually moving apart the first and second lengths of wire;

(d) drawing together portions of the gastrointestinal tract wherein anastomosis is desired, such that the portions are in adjacent, side-by-side relationship, at least one of the portions being open-ended;

(e) forming punctures in walls of the gastrointestinal tract adjacent to each other;

(f) introducing the clip through the punctures, such that the first and second lengths of wire are situated equidistant from the walls, the third length of wire extending across the middle of the punctures;

(g) maintaining the relative positions of the portions of the gastrointestinal tract and the clip in relation thereto, while raising the temperature of the clip to a temperature above its phase transition temperature, such that the elasticity of the clip causes the first and second lengths of wire to converge and to press the aligned portions of the gastrointestinal tract tightly against each other; and (h) surgically sealing the open ends of the portions of the gastrointestinal tract.

BRIEF DESCRIPTION OF THE DRAWINGS

The present invention will be more fully understood and appreciated from the following detailed description, in which:

FIG. 1A is a pictorial illustration of a surgical clip according to a first embodiment of the present invention;

FIG. 1B is a side view of the surgical clip shown in FIG. 1A;

FIG. 1C is a bottom view of the surgical clip shown in FIG. 1A;

FIG. 2A is a pictorial illustration of a surgical clip according to a second embodiment of the present invention;

FIG. 2B is a side view of the surgical clip shown in FIG. 2A;

FIG. 2C is a top view of the surgical clip shown in FIG. 2A;

DETAILED DESCRIPTION OF THE INVENTION

Figure 3:
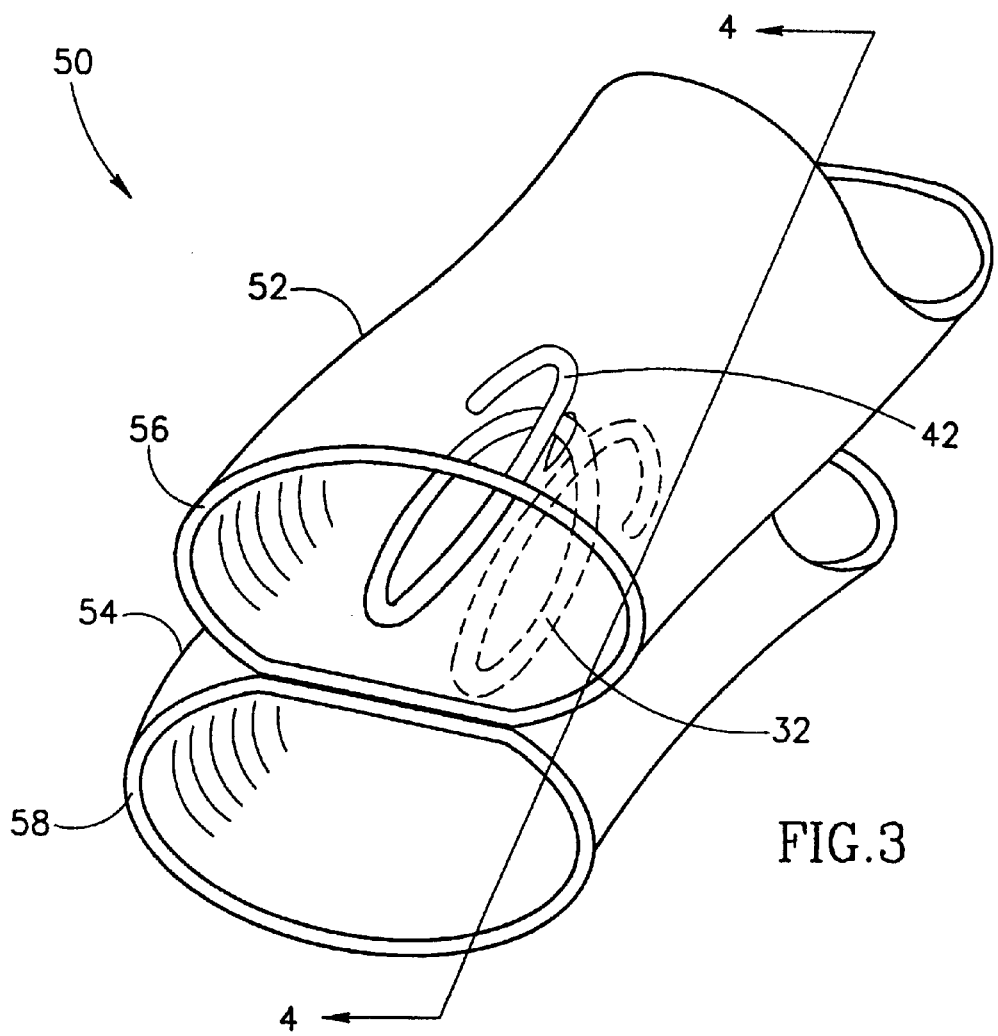
FIG. 3 is a pictorial illustration of a hollow organ inside which there has been placed the surgical clip of FIGS. 2A, B, and C, in accordance with the present invention, the surgical clip being in a plastic state.

The present invention seeks to provide a surgical clip, and a method of use thereof, formed of a shape memory alloy, such as is known in the art, and which provides organ tissue compression along the entire periphery of the clip, thereby to ensure satisfactory joining or anastomosis of a punctured organ.

Referring now to the drawings, FIGS. 1A, 1B, and 1C illustrate a surgical clip, referenced generally 10, according to a first embodiment of the present invention. Clip 10 is typically wire-like, formed of a shape memory alloy, and configured so as to include a pair of loops 12 and 22 joined by a section 18, section 18 being located inside the area surrounded by loops 12 and 22. Loop 12 has first and second ends 14 and 16 respectively, and loop 22 has first and second ends 24 and 26, respectively. Thus, section 18 joins second end 16 of loop 12 to second end 26 of loop 22.

Clip 10 is configured such that, if one were to follow the curve of the clip from first end 14 of loop 12 to first end 24 of loop 22, it would be apparent that there is an S-shaped portion of the clip 10 starting at second end 16 of loop 12, including section 18, and ending at second end 26 of loop 22.

FIGS. 2A, 2B, and 2C illustrate a surgical clip, referenced generally 30, according to a second embodiment of the present invention. Clip 30 is similar to clip 10 (FIGS. 1A, 1B, and 1C) in that it is typically wire-like, formed of a shape memory alloy, and configured so as to include a pair of loops 32 and 42 joined by a section 38, section 38 being located inside the area surrounded by loops 32 and 42. Loop 32 has first and second ends 34 and 36 respectively, and loop 42 has first and second ends 44 and 46 respectively. Thus, section 38 joins second end 36 of loop 32 to second end 46 of loop 42.

The configuration of clip 30 differs from that of clip 10 in that, if one were to follow the curve of the clip 30, from first end 34 of loop 32 to first end 44 of loop 42, it would be apparent that there is a C-shaped portion of the clip 30 starting at second end 36 of loop 32, including section 38, and ending at second end 46 of loop 42.

It will be appreciated that further embodiments of the present invention are possible by providing clips, similar in configuration to clip 30, wherein section 38 is closer to or further from the right end (as viewed in FIG. 2A) of the clip 30. Yet further embodiments of the present invention may be provided by forming clips which are mirror images of clips 10 and 30.

Figure 4:
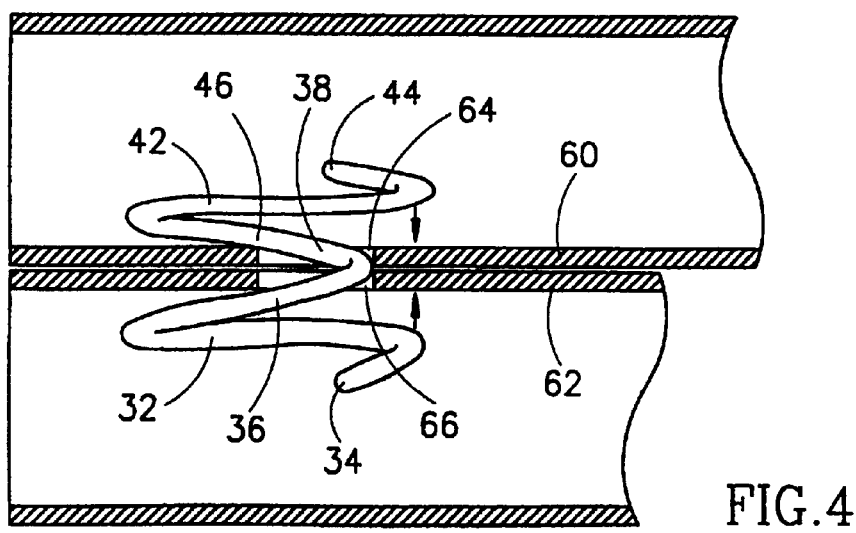
FIG. 4 is a cross-sectional view, taken in the direction of line 4—4, of the hollow organ and surgical clip shown in FIG. 3.
Figure 5:
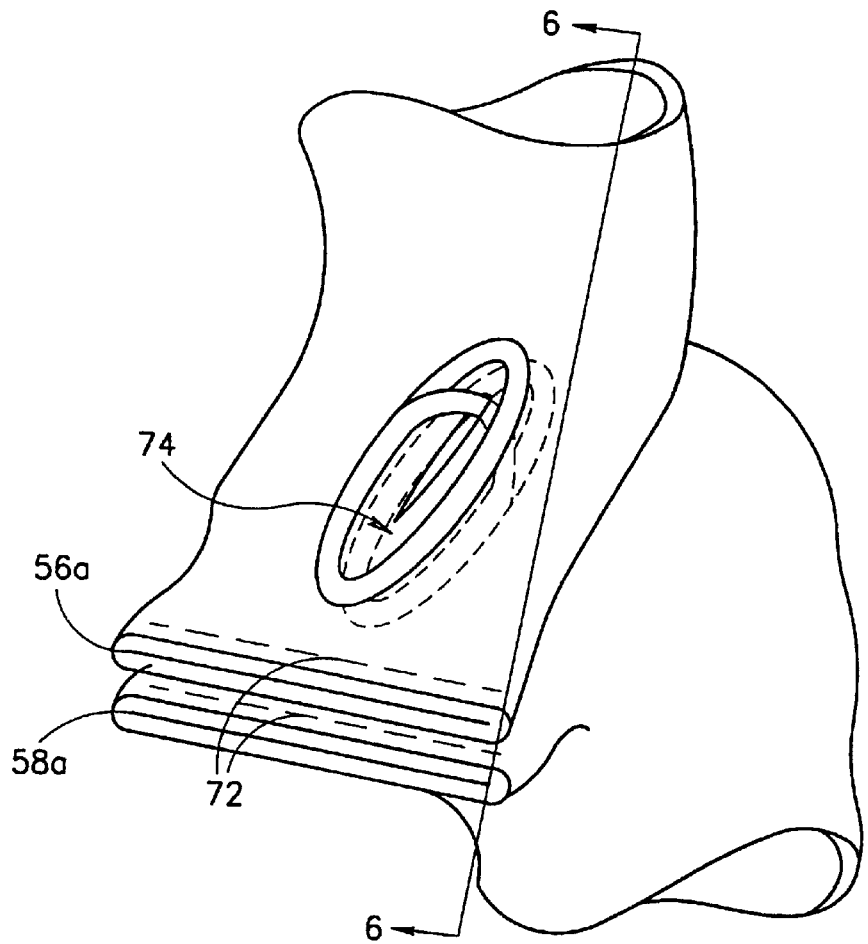
FIG. 5 is a view of the hollow organ and surgical clip shown in FIG. 3, the surgical clip being in an elastic state.
Figure 6:
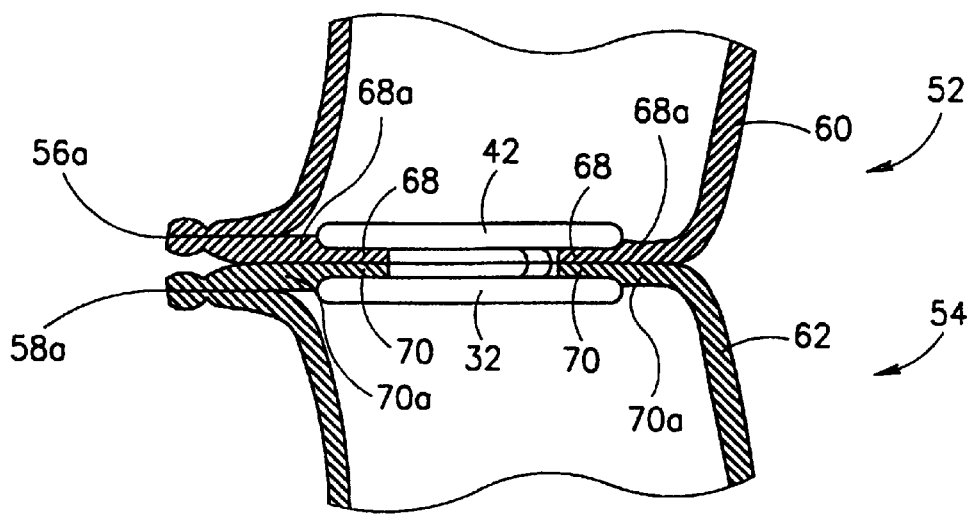
FIG. 6 is a cross-sectional view, taken in the direction of line 6—6, of the hollow organ and surgical clip shown in FIG. 5.

With reference to FIGS. 3 and 4, there are shown portions 52 and 54 of a hollow organ 50, which it is desired to join together by anastomosis, as shown in FIGS. 5 and 6. The method of the present invention will now be described with reference to clip 30. However, it will be appreciated by persons skilled in the art that the method of the present invention may be carried out by utilizing any embodiment of the clip in accordance with the present invention, such as clip 10.

Clip 30 is cooled until it reaches its lower phase transition temperature, as known in the art, the clip 30 thus being in a plastic state. The phase transition temperature may be generally any temperature above −273° C., although more generally it is approximately 25–35° C. below body temperature, preferably approximately 0° C. Loops 32 and 42 are manually moved apart a desired distance and clip 30 is preserved in the cooled state for as long as required until insertion into the organ 50. As shown in FIGS. 3 and 4, portions 52 and 54 of organ 50 are drawn together in an adjacent, side-by-side relationship, and adjacent walls 60 and 62 are held together and are perforated at punctures 64 and 66 (FIG. 4), respectively. Clip 30 is introduced, via open end 56 of portion 52, through punctures 64 and 66, and is held in position inside portions 52 and 54 such that loops 42 and 32 are situated so as to straddle respective walls 60 and 62, section 38 extending across the middle of punctures 64 and 66. It will be appreciated that, alternately, clip 30 may be introduced first into portion 54 and then into portion 52, the same spatial relationship being achieved between the clip 30 and portions 52 and 54 of organ 50. Additionally, while the method of the present invention is described herein in relation to FIGS. 3–6, wherein both organ portions 52 and 54 are open-ended, it will be understood by persons skilled in the art that it is sufficient for either one, and not both, of the organ portions to be open-ended, thus enabling introduction of the clip into the punctures.

The relative positions of portions 52 and 54 of organ 50 and the relative position of clip 30 in relation thereto must be maintained for a period of time during which the temperature of organ 50 is effective to cause the temperature of the clip 30 to rise to a temperature at least equal to its upper phase transition temperature, which, preferably, is body temperature. During the time that the temperature of clip 30 rises towards its transition temperature, loops 32 and 42 continue to converge and to press the tissue portions 70 and 68 of organ walls 62 and 60 located therebetween more and more tightly against each other. Tissue portions 70 and 68 are defined by the portions of walls 62 and 60 located between loops 32 and 42. Thus, each of tissue portions 70 and 68 is configured as an area similar in shape and size to the loops 32 and 42 of clip 30, and each of tissue portions 70 and 68 includes a respective puncture 66 and 64.

The rate by which the temperature of clip 30 rises may be accelerated by heating clip 30, for example, by any method known in the art.

Once the temperature of clip 30 has risen above its transition temperature, clip 30 has returned to its elastic phase, as shown in FIGS. 5 and 6, and maintains walls 60 and 62 in a fixed position relative to each other, with their respective punctures 64 and 66 (FIG. 4) in alignment. Open ends 56 and 58 of portions 52 and 54 may then be surgically sewn closed, as by sutures 72, thereby resulting in closed ends 56a and 58a. Once this has been accomplished, the only pathway from portion 52 to portion 54 of organ 50 is via punctures 64 and 66. The punctures 64 and 66 may be widened somewhat, although they should not be widened to the entire area of tissue portions 68 and 70. Widening of the punctures will create initial patency of the gastrointestinal tract, by approximating the puncture size to the normal size of the gastrointestinal tract.

Due to the pressure exerted by clip 30 on walls 60 and 62 of organ 50, respective tissue portions 68 and 70 are pressed so tightly against each other that blood flow to these tissue portions ceases, resulting in eventual necrosis of these tissue portions 68 and 70. As tissue portions 68 and 70 die, the tissue portions 68a and 70a immediately thereoutside mend together such that portions 52 and 54 of organ 50 are joined, and organ 50 may function as one continuous organ. Once tissue portions 70 and 68 die, they, together with clip 30, become separated from walls 62 and 60, resulting in a hole 74 (FIG. 5). Dead tissue portions 70 and 68, together with clip 30 are passed out of organ 50, via hole 74, by the normal activity of the organ. For example, if organ 50 is the small intestine, and the direction of peristalsis is from portion 52 towards portion 54, then clip 30 and tissue portions 70 and 68 will be passed through portion 54 by the normal activity of the small intestine.

It will be appreciated by persons skilled in the art that there is a direct relationship between the size and shape of the clip used in the surgical procedure described above and the size and shape of the resulting hole in the organ. It is thus possible to chose to perform the procedure with a clip of a particular size and shape so as to achieve a hole of a desired size and shape.

It will be appreciated by persons skilled in the art that the present invention is not limited by what has been shown and described hereinabove, merely by way of illustrative example. Rather, the scope of the present invention is limited solely by the claims, which follow:

What is claimed is:

1. A surgical clip which comprises:
 a first length of a wire formed of a shape memory alloy and having first and second end portions which overlap so as to form a closed geometrical shape having a central opening;
 a second length of a wire formed of said shape memory alloy and having first and second end portions which overlap so as to form a closed geometrical shape similar in configuration and magnitude to said first length of wire, wherein, when placed in side-by-side registration, said first and second lengths of wire fully overlap but said second end portion of said first length of wire and said second end portion of said second length of wire do not overlap; and
 a third length of a wire of said shape memory alloy and formed integrally with said second end portions of said first and second lengths of wire thereby to extend across said central opening so as to connect together said first and second lengths of wire;
 wherein when at a first temperature above a first predetermined temperature, said first and second lengths of wire are positioned in a side-by-side closed position and said shape memory alloy is in an elastic state, and further, when at a second temperature below a second predetermined temperature, below said first temperature, said shape memory alloy is in a plastic state, thereby enabling said first and second lengths of wire to be moved into and to retain a spaced apart position, and upon heating of said clip to a temperature at least equal to said first temperature, said first and second lengths of wire return to said side-by-side closed position, thereby to apply a compressive force to tissue located therebetween.

2. The surgical clip according to claim 1, wherein said geometrical shape is an ellipse.

3. The surgical clip according to claim 1, wherein an S-shaped length is defined by said second end of said first length of wire, said third length of wire, and said second end of said second length of wire.

4. The surgical clip according to claim 1, wherein a C-shaped length is defined by said second end of said first length of wire, said third length of wire, and said second end of said second length of wire.

5. The surgical clip according to claim 4, wherein the area defined by said C-shaped length of wire is less than half the area defined by the first length of wire.

6. The surgical clip according to claim 4, wherein the area defined by said C-shaped length of wire is at least half the area defined by the first length of wire.

7. A method for anastomosing a gastrointestinal tract, said method comprising the following steps:

(a) providing a surgical clip which comprises:
a first length of wire formed of a shape memory alloy and having first and second end portions which overlap so as to form a closed geometrical shape having a central opening;
a second length of a wire formed of the shape memory alloy and having first and second end portions which overlap so as to form a closed geometrical shape similar in configuration and magnitude to the first length of wire, wherein, when placed in side-by-side registration, the first and second lengths of wire fully overlap but the second end portion of said first length of wire and said second end portion of said second length of wire do not overlap; and
a third length of a wire of the shape memory alloy and formed integrally with the second end portions of the first and second lengths of wire thereby to extend across the central opening so as to connect together the first and second lengths of wire;
wherein when at a first temperature above a first predetermined temperature, the first and second lengths of wire are positioned in a side-by-side closed position and the shape memory alloy is in an elastic state, and further, when at a second temperature below a second predetermined temperature, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-by-side close position, thereby to apply a compressive force to tissue located therebetween;

(b) cooling the clip to a temperature below its lower phase transition temperature;

(c) manually moving apart the first and second lengths of wire;

(d) drawing together portions of the gastrointestinal tract wherein anastomosis is desired, such that the portions are in adjacent, side-by-side relationship, at least one of the portions being open-ended;

(e) forming punctures in walls of the gastrointestinal tract adjacent to each other;

(f) introducing the clip through the punctures, such that the first and second lengths of wire are situated equidistant from the walls, the third length of wire extending across the middle of the punctures;

(g) maintaining the relative positions of the portions of the gastrointestinal tract and the clip in relation thereto, while raising the temperature of the clip to a temperature above its upper phase transition temperature, such that the elasticity of the clip causes the first and second lengths of wire to converge and to press the aligned portions of the gastrointestinal tract tightly against each other; and (h) surgically sealing the open ends of the portions of the gastrointestinal tract.

8. A method for anastomosing a gastrointestinal tract according to claim 7, wherein in said step (g), the temperature of the clip is raised to the temperature above its upper phase transition temperature by the heat of the gastrointestinal tract.

9. A method for anastomosing a gastrointestinal tract according to claim 7, including the additional step of:

(i) widening the punctures so as to create initial patency of the gastrointestinal tract.

10. A method for anastomosing a gastrointestinal tract according to claim 7, wherein the geometrical shape is an ellipse.

11. A method for anastomosing a gastrointestinal tract according to claim 7, wherein an S-shaped length is defined by the second end of the first length of wire, the third length of wire, and the second end of the second length of wire.

12. A method for anastomosing a gastrointestinal tract according to claim 7, wherein a C-shaped length is defined by the second end of the first length of wire, the third length of wire, and the second end of the second length of wire.

13. A method for anastomosing a gastrointestinal tract according to claim 12, wherein the area defined by the C-shaped length of wire is less than half the area defined by the first length of wire.

14. A method for anastomosing a gastrointestinal tract according to claim 12, wherein the area defined by the C-shaped length of wire is at least half the area defined by the first length of wire.

* * * * *